(12) United States Patent
Choo et al.

(10) Patent No.: US 6,733,970 B2
(45) Date of Patent: May 11, 2004

(54) SCREENING SYSTEM FOR ZINC FINGER POLYPEPTIDES FOR A DESIRED BINDING ABILITY

(75) Inventors: Yen Choo, Cambridge (GB); Michael Moore, Amersham Bucks (GB)

(73) Assignee: Gendaq Limited, London (GB)

(*) Notice: Subject to any disclaimer, the term of this patent is extended or adjusted under 35 U.S.C. 154(b) by 298 days.

(21) Appl. No.: 09/851,271

(22) Filed: May 8, 2001

(65) Prior Publication Data

US 2002/0064824 A1 May 30, 2002

Related U.S. Application Data

(63) Continuation-in-part of application No. PCT/GB99/03730, filed on Nov. 9, 1999.

(30) Foreign Application Priority Data

Nov. 9, 1998 (GB) .............................................. 9824544

(51) Int. Cl.[7] .......................... C12Q 1/68; C12N 15/64
(52) U.S. Cl. ...................... 435/6; 435/69.1; 435/91.41; 435/91.51
(58) Field of Search ........................ 435/6, 69.1, 91.41, 435/91.45

(56) References Cited

U.S. PATENT DOCUMENTS

| | | |
|---|---|---|
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid |
| 5,350,840 A | 9/1994 | Call et al. |
| 5,356,802 A | 10/1994 | Chandrasegaran |
| 5,376,530 A | 12/1994 | De the et al. |
| 5,403,484 A | 4/1995 | Ladner et al. |
| 5,436,150 A | 7/1995 | Chandrasegaran |
| 5,487,994 A | 1/1996 | Chandrasegaran |
| 5,498,530 A | 3/1996 | Schatz et al. |
| 5,789,538 A | 8/1998 | Rebar et al. |
| 5,792,640 A | 8/1998 | Chandrasegaran |
| 5,830,721 A | 11/1998 | Stemmer et al. |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,939,538 A | 8/1999 | Leavitt et al. |
| 5,972,615 A | 10/1999 | An et al. |
| 6,001,885 A | 12/1999 | Vega et al. |
| 6,007,988 A | 12/1999 | Choo et al. |
| 6,013,453 A | 1/2000 | Choo et al. |

FOREIGN PATENT DOCUMENTS

| | | |
|---|---|---|
| EP | 0 875 567 A2 | 11/1998 |
| WO | WO 96/06110 | 2/1996 |
| WO | WO 96/11267 | 4/1996 |
| WO | WO 96/20951 | 7/1996 |
| WO | WO 97/27212 | 7/1997 |
| WO | WO 97/27213 | 7/1997 |
| WO | WO 98/53057 | 11/1998 |
| WO | WO 98/53058 | 11/1998 |
| WO | WO 98/53060 | 11/1998 |
| WO | WO 98/54311 | 12/1998 |
| WO | WO 99/36553 | 7/1999 |
| WO | WO 99/41371 | 8/1999 |
| WO | WO 99/42474 A2 | 8/1999 |
| WO | WO 99/45132 | 9/1999 |
| WO | Wo 99/48909 | 9/1999 |
| WO | WO 00/23464 A2 | 4/2000 |
| WO | WO 00/27878 | 5/2000 |

OTHER PUBLICATIONS

Berg, "Proposed structure for the zinc–binding domains from transcription factor IIIA and realted proteins," *Proc Nail Acad Sci U S A* 85 (1):99–102, 1998.

Elrod–Erickson et al., "Zif268 protein–DNA complex refined at 1.6 A: a model system for understanding zinc finger–DNA interactions," *Structure* 4:1171–1180, 1996.

Miller et al., "Repetitive zinc–binding domains in the protein transcription factor IIIA from Xenopus oocytes," *EMBO J.* 4:1609–1614, 1985.

*Primary Examiner*—John S. Brusca
(74) *Attorney, Agent, or Firm*—Robins & Pasternak LLP; Sean M. Brennan

(57) ABSTRACT

This invention relates to a method for producing a zinc finger nucleic acid binding protein comprising preparing a zinc finger protein according design rules, varying the protein at one or more positions, and selecting variants which bind to a target nucleic acid sequence by polysome display.

13 Claims, No Drawings

SEQUENCE LISTING

```
<160> NUMBER OF SEQ ID NOS: 16

<210> SEQ ID NO 1
<211> LENGTH: 264
<212> TYPE: DNA
<213> ORGANISM: Artificial Sequence
<220> FEATURE:
<221> NAME/KEY: misc_structure
<222> LOCATION: (1)..(264)
<223> OTHER INFORMATION: sequence coding for a zinc finger protein

<400> SEQUENCE: 1
gcagaagaga agccttttca gtgtcgaatc tgcatgcgta acttcagcga tcgtagtagt        60
cttacccgcc acacgaggac ccacacaggc gagaagcctt ttcagtgtcg aatctgcatg       120
cgtaacttca gcaggagcga taaccttacg agacacctaa ggacccacac aggcgagaag       180
``` cctttttcagt gtcgaatctg catgcgtaac ttcaggcaag ctgatcatct tcaagagcac    240
ctaaagaccc acacaggcga gaag    264

```
<210> SEQ ID NO 2
<211> LENGTH: 88
<212> TYPE: PRT
<213> ORGANISM: Artificial Sequence
<220> FEATURE:
<221> NAME/KEY: ZN_FING
<222> LOCATION: (1)..(88)
<223> OTHER INFORMATION: protein sequence encoding a zinc-finger domain

<400> SEQUENCE: 2
```

Ala Glu Glu Lys Pro Phe Gln Cys Arg Ile Cys Met Arg Asn Phe Ser
1               5                   10                  15

Asp Arg Ser Ser Leu Thr Arg His Thr Arg Thr His Thr Gly Glu Lys
            20                  25                  30

Pro Phe Gln Cys Arg Ile Cys Met Arg Asn Phe Ser Arg Ser Asp Asn
        35                  40                  45

Leu Thr Arg His Leu Arg Thr His Thr Gly Glu Lys Pro Phe Gln Cys
    50                  55                  60

Arg Ile Cys Met Arg Asn Phe Arg Gln Ala Asp His Leu Gln Glu His
65                  70                  75                  80

Leu Lys Thr His Thr Gly Glu Lys
                85

```
<210> SEQ ID NO 3
<211> LENGTH: 31
<212> TYPE: PRT
<213> ORGANISM: Artificial Sequence
<220> FEATURE:
<223> OTHER INFORMATION: Sequence of the Zince Finger Framework
<221> NAME/KEY: UNSURE
<222> LOCATION: (1)..(31)
<223> OTHER INFORMATION: 'X' can be any amino acid as described in the
      specification

<400> SEQUENCE: 3
```

Xaa Xaa Cys Xaa Xaa Xaa Xaa Xaa Cys Xaa Xaa Xaa Xaa Xaa Xaa Xaa
1               5                   10                  15

Xaa Xaa Xaa Xaa Xaa Xaa Xaa His Xaa Xaa Xaa Xaa Xaa Xaa His
            20                  25                  30

```
<210> SEQ ID NO 4
<211> LENGTH: 31
<212> TYPE: PRT
<213> ORGANISM: Artificial Sequence
<220> FEATURE:
<223> OTHER INFORMATION: Sequence of the Zince Finger Framework
<221> NAME/KEY: UNSURE
<222> LOCATION: (1)..(31)
<223> OTHER INFORMATION: 'X' can be any amino acid as described in the
      specification

<400> SEQUENCE: 4
```

Xaa Xaa Cys Xaa Xaa Xaa Xaa Xaa Cys Xaa Xaa Xaa Xaa Xaa Xaa Xaa
1               5                   10                  15

Xaa Xaa Xaa Xaa Xaa Xaa Xaa His Xaa Xaa Xaa Xaa Xaa Xaa Cys
            20                  25                  30

```
<210> SEQ ID NO 5
<211> LENGTH: 24
<212> TYPE: PRT
```

```
<213> ORGANISM: Artificial Sequence
<220> FEATURE:
<223> OTHER INFORMATION: Sequence of the Zinc Finger Nucleic Acid
      Binding Motifs
<221> NAME/KEY: UNSURE
<222> LOCATION: (1)..(24)
<223> OTHER INFORMATION: 'X' can be any amino acid as described in the
      specification

<400> SEQUENCE: 5

Xaa Cys Xaa Xaa Xaa Xaa Cys Xaa Xaa Xaa Phe Xaa Xaa Xaa Xaa Xaa
1               5                   10                  15

Leu Xaa Xaa His Xaa Xaa Xaa His
            20

<210> SEQ ID NO 6
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: linker

<400> SEQUENCE: 6

Thr Gly Glu Lys
1

<210> SEQ ID NO 7
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: linker

<400> SEQUENCE: 7

Thr Gly Glu Lys Pro
1               5

<210> SEQ ID NO 8
<211> LENGTH: 26
<212> TYPE: PRT
<213> ORGANISM: Artificial Sequence
<220> FEATURE:
<221> NAME/KEY: ZN_FING
<222> LOCATION: (1)..(26)
<223> OTHER INFORMATION: zinc finger consensus structure

<400> SEQUENCE: 8

Pro Tyr Lys Cys Pro Glu Cys Gly Lys Ser Phe Ser Gln Lys Ser Asp
1               5                   10                  15

Leu Val Lys His Gln Arg Thr His Thr Gly
            20                  25

<210> SEQ ID NO 9
<211> LENGTH: 29
<212> TYPE: PRT
<213> ORGANISM: Artificial Sequence
<220> FEATURE:
<221> NAME/KEY: ZN_FING
<222> LOCATION: (1)..(29)
<223> OTHER INFORMATION: zinc finger consensus structure

<400> SEQUENCE: 9

Pro Tyr Lys Cys Ser Glu Cys Gly Lys Ala Phe Ser Gln Lys Ser Asn
1               5                   10                  15
```

Leu Thr Arg His Gln Arg Ile His Thr Gly Glu Lys Pro
            20                  25

<210> SEQ ID NO 10
<211> LENGTH: 6
<212> TYPE: PRT
<213> ORGANISM: Artificial Sequence
<220> FEATURE:
<221> NAME/KEY: PEPTIDE
<222> LOCATION: (1)..(6)
<223> OTHER INFORMATION: leader peptide

<400> SEQUENCE: 10

Met Ala Glu Glu Lys Pro
1               5

<210> SEQ ID NO 11
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: smallest unit of stalling polypeptide sequence

<400> SEQUENCE: 11

Ala Ala Val Pro
1

<210> SEQ ID NO 12
<211> LENGTH: 24
<212> TYPE: PRT
<213> ORGANISM: Artificial Sequence
<220> FEATURE:
<221> NAME/KEY: PEPTIDE
<222> LOCATION: (1)..(24)
<223> OTHER INFORMATION: linker sequence followed by the stalling
      polypeptide sequence

<400> SEQUENCE: 12

Gly Gly Gly Gly Ser Gly Gly Gly Ser Gly Gly Gly Ser Gly
1               5                   10                  15

Gly Gly Ser Ala Ala Val Pro
            20

<210> SEQ ID NO 13
<211> LENGTH: 23
<212> TYPE: DNA
<213> ORGANISM: Artificial Sequence
<220> FEATURE:
<221> NAME/KEY: promoter
<222> LOCATION: (1)..(23)
<223> OTHER INFORMATION: bacteriophage T7 RNA polymerase promoter
      sequence

<400> SEQUENCE: 13
taatacgact aactataggg aga                                         23

<210> SEQ ID NO 14
<211> LENGTH: 6
<212> TYPE: DNA
<213> ORGANISM: Artificial Sequence
<220> FEATURE:
<221> NAME/KEY: RBS
<222> LOCATION: (1)..(6)
<223> OTHER INFORMATION: bacteriophage T7, gene 10 ribosome binding site

<400> SEQUENCE: 14

```
aaggag                                                                  6

<210> SEQ ID NO 15
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: DNA sequence encoding the ribosome stalling
      peptide sequence

<400> SEQUENCE: 15
atggttaaaa cagataaa                                                    18

<210> SEQ ID NO 16
<211> LENGTH: 6
<212> TYPE: PRT
<213> ORGANISM: Artificial Sequence
<220> FEATURE:
<221> NAME/KEY: PEPTIDE
<222> LOCATION: (1)..(6)
<223> OTHER INFORMATION: ribosome stalling peptide sequence

<400> SEQUENCE: 16

Met Val Lys Thr Asp Lys
1               5
```

SCREENING SYSTEM FOR ZINC FINGER POLYPEPTIDES FOR A DESIRED BINDING ABILITY

REFERENCE TO RELATED APPLICATIONS/ INCORPORATION BY REFERENCE

This application is a continuation-in-part of PCT application no. PCT/GB99/03730 entitled "SCREENING SYSTEM FOR ZINC FINGER POLYPEPTIDES FOR A DESIRED BINDING ABILITY" filed Nov. 9, 1999, published as WO 00/27878A1 on May 18, 2000 designating the US and claiming priority from GB application 9824544.2 filed Nov. 9, 1998.

Reference is made to: U.S. application Ser. No. 09/732, 348, filed Dec. 7, 2000; U.S. application Ser. No. 09/718, 538, filed Nov. 22, 2000; U.S. application Ser. No. 09/139, 672, filed Aug. 25 1998 (now U.S. Pat. No. 6,013,453), which is a continuation of U.S. application Ser. No. 08/793, 408 (now U.S. Pat. No. 6,007,988), filed as PCT application no. PCT/GB95/01949 on Aug. 17, 1995, designating the U.S. and, published as WO 96/06166 on Feb. 29, 1996 ("Improvements In or Relating to Binding Proteins For Recognition of DNA"); PCT/GB95/01949 claims the benefit of priority from UK application 9514698.1, filed Jul. 19, 1995, UK application 9422534.9, filed Nov. 8, 1994 and UK application 9146880.4, filed Aug. 20, 1994. Mention is also made of: U.S. Ser. No. 08/422,107; WO 96/32475; WO 99/47656A2, published Sep. 23, 1999 ("Nucleic Acid Binding Proteins"); WO 98/53060A1, published Nov. 26, 1998 ("Nucleic Acid Binding Proteins"); WO 98/53059A1 published Nov. 26, 1998 ("Nucleic Acid Binding Proteins"); WO 98/53058A1 published Nov. 26, 1998 ("Nucleic Acid Binding Proteins"); WO 98/53057A1 published Nov. 26, 1998 ("Nucleic Acid Binding Polypeptide Library"); and, U.S. Pat. Nos. 6,013,453 and 6,007,988.

Each of the foregoing applications and patents, and each document cited or referenced in each of the foregoing applications and patents, including during the prosecution of each of the foregoing applications and patents ("application cited documents"), and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

The present application relates to a method for screening zinc finger polypeptides for a desired binding ability. In particular, the invention relates to a polysome display technique which permits the isolation of binding polypeptides without resorting to phage display techniques.

Protein-nucleic acid recognition is a commonplace phenomenon which is central to a large number of biomolecular control mechanisms which regulate the functioning of eukaryotic and procaryotic cells. For instance, protein-DNA interactions form the basis of the regulation of gene expression and are thus one of the subjects most widely studied by molecular biologists.

A wealth of biochemical and structural information explains the details of protein-DNA recognition in numerous instances, to the extent that general principles of recognition have emerged. Many DNA-binding proteins contain independently folded domains for the recognition of DNA, and these domains in turn belong to a large number of structural families, such as the leucine zipper, the "helix-turn-helix" and zinc finger families.

Most sequence-specific DNA-binding proteins bind to the DNA double helix by inserting an α-helix into the major groove (Pabo & Sauer 1992 Annu. Rev. Biochem. 61, 1053–1095; Harrison 1991 Nature (London) 353, 715–719; and Klug 1993 Gene 135, 83–92). Sequence specificity results from the geometrical and chemical complementarity between the amino acid side chains of the α-helix and the accessible groups exposed on the edges of base-pairs. In addition to this direct reading of the DNA sequence. interactions with the DNA backbone stabilise the complex and are sensitive to the conformation of the nucleic acid, which in turn depends on the base sequence (Dickerson & Drew 1981 J. Mol. Biol. 149, 761–786. Crystal structures of protein-DNA complexes have shown that proteins can be idiosyncratic in their mode of DNA recognition, at least partly because they may use alternative geometries to present their sensory α-helices to DNA, allowing a variety of different base contacts to be made by a single amino acid and vice versa (Matthews 1988 Nature (London) 335, 294–295).

Protein engineering experiments have shown that it is possible to alter rationally the DNA-binding characteristics of individual zinc fingers when one or more of the α-helical positions is varied in a number of proteins (Nardelli et al., 1991 Nature (London) 349, 175–178; Nardelli et al. 1992 Nucleic Acids Res. 20, 4137–4144; and Desjarlais & Berg 1992a Proteins 13, 272). It has already been possible to propose some principles relating amino acids on the α-helix to corresponding bases in the bound DNA sequence (Desjarlais & Berg 1992b Proc. Natl. Acad. Sci. USA 89, 7345–7349). However in this approach the altered positions on the α-helix are prejudged, making it possible to overlook the role of positions which are not currently considered important; and secondly, owing to the importance of context, concomitant alterations are sometimes required to affect specificity (Desjarlais & Berg 1992b), so that a significant correlation between an amino acid and base may be misconstrued.

More sophisticated principles describing the relationship between the sequence of the zinc finger and the nucleic acid target have been described, for example in WO 96/06166 (Medical Research Council).

To investigate binding of mutant Zf proteins, Thiesen and Bach (1991 FEBS 283, 23–26) mutated Zf fingers and studied their binding to randomised oligonucleotides, using electrophoretic mobility shift assays. Subsequent use of phage display technology has permitted the expression of random libraries of Zf mutant proteins on the surface of bacteriophage. The three Zf domains of Zif268, with 4 positions within finger one randomised, have been displayed on the surface of filamentous phage by Rebar and Pabo (1994 Science 263, 671–673). The library was then subjected to rounds of affinity selection by binding to target DNA oligonucleotide sequences in order to obtain Zf proteins with new binding specificities. Randomised mutagenesis (at the same postions as those selected by Rebar & Pabo) of finger 1 of Zif 268 with phage display has also been used by Jamieson et al., (1994 Biochemistry 33, 5689–5695) to create novel binding specificity and affinity.

In summary, it is known that Zf protein motifs are widespread in DNA binding proteins and that binding is via three key amino acids, each one contacting a single base pair in the target DNA sequence. Motifs are modular and may be linked together to form a set of fingers which recognise a contiguous DNA sequence (e.g. a three fingered protein will recognise a 9 mer etc). The key residues involved in DNA binding have been identified through sequence data and from structural information. Directed and random mutagenesis has confirmed the role of these amino acids in determining specificity and affinity. Phage display has been used to screen for new binding specificities of random mutants of fingers. Therefore, the combination of a set of rules with a selection process appears to provide the most promising avenue for the development of zinc finger proteins.

SUMMARY OF THE INVENTION

According to a first aspect of, the present invention, there is provided a method for producing a zinc finger nucleic acid binding protein comprising preparing a zinc finger protein according design rules, varying the protein at one or more positions, and selecting variants which bind to a target nucleic acid sequence by polysome display.

According to a second aspect of the present invention, there is provided a method for producing a zinc finger nucleic acid binding protein comprising an at least partially varied sequence and selecting variants thereof which bind to a target DNA strand, comprising the steps of:

(i) preparing a nucleic acid binding protein of the Cys2-His2 zinc finger class capable of binding to a nucleic acid triplet in a target nucleic acid sequence, wherein binding to each base of the triplet by an cc-helical zinc finger nucleic acid binding motif in the protein is determined as follows:
  a) if the 5' base in the triplet is G, then position +6 in the α-helix is Arg; or position +6 is Ser or Thr and position ++2 is Asp;
  b) if the 5' base in the triplet is A, then position +6 in the α-helix is Gln and ++2 is not Asp;
  c) if the 5' base in the triplet is T, then position +6 in the α-helix is Ser or Thr and position ++2 is Asp;
  d) if the 5' base in the triplet is C, then position +6 in the α-helix may be any amino acid, provided that position ++2 in the α-helix is not Asp;
  e) if the central base in the triplet is G, then position +3 in the α-helix is His,
  f) if the central base in the triplet is A, then position +3 in the α-helix is Asn;
  g) if the central base in the triplet is T, then position +3 in the α-helix is Ala. Ser, or Val; provided that if it is Ala, then one of the residues at −1 or +6 is a small residue;
  h) if the central base in the triplet is C, then position +3 in the α-helix is Ser, Asp, Glu, Leu, Thr or Val;
  i) if the 3' base in the triplet is G, then position −1 in the α-helix is Arg;
  j) if the 3' base in the triplet is A, then position −1 in the α-helix is Gln;
  k) if the 3' base in the triplet is T, then position −1 in the α-helix is Asn or Gln;
  l) if the 3' base in the triplet is C, then position −1 in the α-helix is Asp;

(ii) varying the resultant polypeptide at at least one position; and (iii) selecting the variants which bind to a target nucleic acid sequence by polysome display.

SEQ ID NOs: are assigned as follows:
SEQ ID NO:1
Nucleotide sequence encoding the zinc finger protein;
SEQ ID NO:2
Amino acid sequence of the zinc finger protein;
SEQ ID NO:3
Sequence of the zinc finger framework as described page 6 lines 21–24 of the specification
XXCXXXXXCX XXXXXXXXXX XXXHXXXXXX H
SEQ ID NO:4
Alternate Sequence of the zinc finger framework as described page 6 lines 21–24 of the specification
XXCXXXXXCX XXXXXXXXXX XXXHXXXXXX C
SEQ ID NO:5
Sequence of the zinc finger nucleic acid binding motifs as described page 7 lines 1–7 of the specification
XCXXXXCXXX FXXXXXLXXH XXXH
SEQ ID NO:6
TGEK
SEQ ID NO:7
TGEKP
SEQ ID NO:8
PYKCPECGKS FSQKSDLVKH QRTHTG
SEQ ID NO:9
PYKCSECGKA FSQKSNLTRH QRIHTGEKP
SEQ ID NO:10
MAEEKP
SEQ ID NO: 11
AAVP
SEQ ID NO: 12
GGGGSGGGGS GGGGSGGGGS AAVP
SEQ ID NO: 13
taatacgact aactataggg aga
SEQ ID NO: 14
aaggag
SEQ ID NO: 15
atggttaaaa cagataaa
SEQ ID No: 16
MVKTDK;

DETAILED DESCRIPTION OF THE INVENTION

All of the nucleic acid-binding residue positions of zinc fingers, as referred to herein, are numbered from the first residue in the α-helix of the finger, ranging from +1 to +9. "−1" refers to the residue in the framework structure immediately preceding the α-helix in a Cys2-His2 zinc finger polypeptide. Residues referred to as "++" are residues present in an adjacent (C-terminal) finger. Where there is no C-terminal adjacent finger. "++" interactions do not operate.

Cys2-His2 zinc finger binding, proteins, as is well known in the art, bind to target nucleic acid sequences via α-helical zinc metal atom coordinated binding, motifs known as zinc fingers. Each zinc finger in a zinc finger nucleic acid binding protein is responsible for determining binding to a nucleic acid triplet in a nucleic acid binding, sequence. Preferably, there are 2or more zinc fingers, for example 2, 3, 4, 5 or 6 zinc fingers, in each binding protein. Advantageously, there are 3zinc fingers in each zinc finger binding protein.

The method of the present invention allows the production of what are essentially artificial nucleic acid binding proteins. In these proteins, artificial analogues of amino acids may be used, to impart the proteins with desired properties or for other reasons. Thus, the term "amino acid", particularly in the context where "any amino acid" is referred to, means any sort of natural or artificial amino acid or amino acid analogue that may be employed in protein construction according to methods known in the art. Moreover, any specific amino acid referred to herein may be replaced by a functional analogue thereof, particularly an artificial functional analogue. The nomenclature used herein therefore specifically comprises within its scope functional analogues of the defined amino acids.

The α-helix of a zinc finger binding protein aligns antiparallel to the nucleic acid strand, such that the primary nucleic acid sequence is arranged 3' to 5' in order to correspond with the N terminal to C-terminal sequence of the zinc finger. Since nucleic acid sequences are conventionally written 5' to 3', and amino acid sequences N-terminus to C-terminus, the result is that when a nucleic acid sequence and a zinc finger protein are aligned according to convention, the primary interaction of the zinc finger is with the −strand of the nucleic acid, since it is this strand which is aligned 3' to 5'. These conventions are followed in the nomenclature used herein. It should be noted, however, that in nature certain fingers, such as finger 4 of the protein GLI, bind to the +strand of nucleic acid: see Suzuki et al., (1994) NAR 22:3397–3405 and Pavletich and Pabo, (1993) Science 261:1701–1707. The incorporation of such fingers into nucleic acid binding) molecules according to the invention is envisaged.

A zinc finger binding motif is a structure well known to those in the art and defined in, for example, Miller et al., (1985) EMBO J. 4:1609–1614; Berg (1988) PNAS (USA) 85:99–102; Lee et al., (1989) Science 245:635–637; see International patent applications WO 96/06166 and WO 96/32475, corresponding to U.S. Ser. No. 08/422,107, incorporated herein by reference.

As used herein, "nucleic acid" refers to both RNA and DNA, constructed from natural nucleic acid bases or synthetic bases, or mixtures thereof. Preferably, however, the binding proteins of the invention are DNA binding proteins.

The structure of the framework of Cys2-His2 zinc fingers is known in the art. The present invention encompasses both those structures which have been observed in nature, including consensus structures derived therefrom, and artificial structures which have non-natural residue numbers and spacing but which retain the functionality of a zinc finger.

In general, a preferred zinc finger framework has the structure:

$$X_{0-2} C\ X_{1-5} C\ X_{9-14} H\ X_{3-6}{}^{K}/C \quad \text{(A)}$$

where X is any amino acid, and the numbers in subscript indicate the possible numbers of residues represented by X.

In a preferred aspect of the present invention, zinc finger nucleic acid binding motifs may be represented as motifs having the following primary structure:

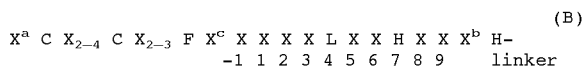

```
                                                    (B)
X^a  C  X_{2-4}  C  X_{2-3}  F  X^c  X  X  X  X  L  X  X  H  X  X  X^b  H-
                            -1  1  2  3  4  5  6  7  8  9          linker
``` wherein X (including $X^a$, $X^b$ and $X^c$) is any amino acid. $X_{2-4}$ and $X_{2-3}$ refer to the presence of 2 or 4, or 2 or 3, amino acids, respectively. The Cys and His residues, which together co-ordinate the zinc metal atom, are marked in bold text and are usually invariant, as is the Leu residue at position +4 in the α-helix.

Modifications to this representation may occur or be effected without necessarily abolishing zinc finger function, by insertion, mutation or deletion of amino acids. For example it is known that the second His residue may be replaced by Cys (Krizek et al., (1991) J. Am. Chem. Soc. 113:4518–4523) and chat Leu at +4 can in some circumstances be replaced with Arg. The Phe residue before $X_c$ may be replaced by any aromatic other than Trp. Moreover, experiments have shown that departure from the preferred structure and residue assignments for the zinc finger are tolerated and may even prove beneficial in binding to certain nucleic acid sequences. Even taking this into account, however, the general structure involving an α-helix coordinated by a zinc atom which contacts four Cys or His residues, does not alter. As used herein, structures (A) and (B) above are taken as an exemplary structure representing all zinc finger structures of the Cys2-His2 type.

Preferably, $X^a$ is $^F/_Y$-X or P-$^F/_Y$-X. In this context, X is any amino acid. Preferably, in this context X is E, K, T or S. Less preferred but also envisaged are Q, V, A and P. The remaining amino acids remain possible.

Preferably, $X_{2-4}$ consists of two amino acids rather than four. The first of these amino acids may be any amino acid, but S, E, K, T, P and R are preferred. Advantageously, it is P or R. The second of these amino acids is preferably E, although any amino acid may be used.

Preferably, $X^b$ is T or I.

Preferably, $X^c$ is S or T.

Preferably, $X_{2-3}$ is G-K-A, G-K-C, G-K-S or G-K-G. However, departures from the preferred residues are possible, for example in the form of M-R-N or M-R.

Preferably, the linker is T-G-E-K or T-G-E-K-P.

As set out above, the major binding interactions occur with amino acids −1, +3 and +6. Amino acids +4 and +7 are largely invariant. The remaining amino acids may be essentially any amino acids. Preferably, position +9 is occupied by Arg or Lys. Advantageously, positions +1, +5 and +8 are not hydrophobic amino acids, that is to say are not Phe, Trp or Tyr. Preferably, position +2 is any amino acid, and preferably serine, save where its nature is dictated by its role as a ++2 amino acid for an N-terminal zinc finger in the same nucleic acid binding molecule.

In a most preferred aspect, therefore, bringing together the above, the invention allows the definition of every residue in a zinc finger nucleic acid binding motif which will bind specifically to a given nucleic acid triplet.

The code provided by the present invention is not entirely rigid; certain choices are provided. For example, positions +1, +5 and +8 may have any amino acid allocation, whilst other positions may have certain options: for example, the present rules provide that, for binding to a central T residue, any one of Ala, Ser or Val may be used at +3. In its broadest sense, therefore, the present invention provides a very large number of proteins which are capable of binding to every defined target nucleic acid triplet. As set forth below, these protein may be selected for binding ability using polysome display techniques.

Preferably, however, the number of possibilities may be significantly reduced before selection. For example, the non-critical residues +1, +5 and +8 may be occupied by the residues Lys, Thr and Gln respectively as a default option. In the case of the other choices, for example, the first-given option may be employed as a default. Thus, the code according to the present invention allows the design of a single, defined polypeptide (a "default" polypeptide) which will bind to its target triplet.

In a further aspect of the present invention, there is provided a method for preparing a nucleic acid binding protein of the Cys2-His2 zinc finger class capable of binding to a target nucleic acid sequence, comprising the steps of:

a) selecting a model zinc finger domain from the group consisting of naturally occurring zinc fingers and consensus zinc fingers;

b) varying at least one of positions −1, +3, +6 (and ++2) the finger as required according to the rules set forth above; and c) selecting the variants which bind to the target nucleic acid by polysome display.

In general, naturally occurring zinc fingers may be selected from those fingers for which the nucleic acid binding specificity is known. For example, these may be the fingers for which a crystal structure has been resolved: namely Zif 268 (Elrod-Erickson et al., (1996) Structure 4:1171–1180), GLI (Pavletich and Pabo, (1993) Science 261:1701–1707), Tramtrack (Fairall et al., (1993) Nature 366:483–487) and YY1 (Houbaviy et al., (1996) PNAS (USA) 93:13577–13582).

The naturally occurring zinc finger 2 in Zif 268 makes an excellent starting point from which to engineer a zinc finger and is preferred.

Consensus zinc finger structures may be prepared by comparing the sequences of known zinc fingers, irrespective of whether their binding domain is known. Preferably, the consensus sequence is selected from the group consisting of the consensus structure P Y K C P E C G K S F S Q K S D L V K H Q R T H T G (SEQ ID NO:8), and the consensus structure P Y K C S E C G K A F S Q K S N L T R H Q R I H T G E K P (SEQ ID NO:9).

The consensuses are derived from the consensus provided by Krizek et al., (1991) J. Am. Chem. Soc. 113:4518–4523 and from Jacobs, (1993) PhD thesis. University of Cambridge, UK. In both cases, the linker sequences described above for joining two zinc finger motifs together, namely TGEK or TGEKP can be formed on the ends of the consensus. Thus, a P may be removed where necessary, or, in the case of the consensus terminating T G, E K (P) can be added.

When the nucleic acid specificity of the model finger selected is known, the mutation of the finger in order to modify its specificity to bind to the target nucleic acid may be directed to residues known to affect binding to bases at which the natural and desired targets differ. Otherwise, mutation of the model fingers should be concentrated upon residues −1, +3, +6 and ++2 as provided for in the foregoing rules.

In order to produce a binding protein having improved binding, moreover, the rules provided by the present invention may be supplemented by physical or virtual modelling of the protein/nucleic acid interface in order to assist in residue selection.

Zinc finger binding motifs designed according to the invention may be combined into nucleic acid binding proteins having a multiplicity of zinc fingers. Preferably, the proteins have at least two zinc fingers. In nature, zinc finger binding proteins commonly have at least three zinc fingers, although two-zinc finger proteins such as Tramtrack are known. The presence of at least three zinc fingers is preferred. Binding proteins may be constructed by joining the required fingers end to end, N-terminus to C-terminus. Preferably, this is effected by joining together the relevant nucleic acid coding sequences encoding the zinc fingers to produce a composite coding sequence encoding the entire binding protein. The invention therefore provides a method for producing a nucleic acid binding protein as defined above, wherein the nucleic acid binding protein is constructed by recombinant DNA technology, the method comprising the steps of:

a) preparing a nucleic acid coding sequence encoding two or more zinc finger binding motifs as defined above, placed N-terminus to C-terminus;

b) inserting the nucleic acid sequence into a suitable expression vector; and c) expressing the nucleic acid sequence in a host organism in order to obtain the nucleic acid binding protein.

A "leader" peptide may be added to the N-terminal finger. Preferably, the leader is MAEEKP (SEQ ID NO:10).

The nucleic acid encoding the nucleic acid binding protein according to the invention can be incorporated into vectors for further manipulation. As used herein, vector (or plasmid) refers to discrete elements that are used to introduce heterologous nucleic acid into cells for either expression or replication thereof. Selection and use of such vehicles are well within the skill of the person of ordinary skill in the art. Many vectors are available, and selection of appropriate vector will depend on the intended use of the vector, i.e. whether it is to be used for DNA amplification or for nucleic acid expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses.

The origin of replication from the plasmid pBR322 is suitable for most Gram-negative bacteria, the $2\mu$ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class or organisms but can be transfected into another organism for expression. For example, a vector is cloned in *E. coli* and then the same vector is transfected into yeast or mammalian cells even rough it is not capable of replicating independently of the host cell chromosome. DNA may also be replicated by insertion into the host genome. However, the recovery of genomic DNA encoding the nucleic acid binding protein is more complex than that of exogenously replicated vector because restriction enzyme digestion is required to excise nucleic acid binding protein DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins. e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript© vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up nucleic acid binding protein nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the 'transformants under conditions in which the pressure is progressively increased, thereby leading to amplification (at its chromosomal integration site) of both the selection gene and the linked DNA that encodes the nucleic acid binding protein. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to nucleic acid binding protein encoding nucleic acid. Such a promoter may be inducible or constitutive. The promoters are operably linked to DNA encoding the nucleic acid binding protein by removing the promoter from the source DNA by restriction enzyme digestion and inserting the isolated promoter sequence into the vector. Both the native nucleic acid binding protein promoter sequence and many heterologous promoters may be used to direct amplification and/or expression of nucleic acid binding protein encoding DNA.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding nucleic acid binding protein, using linkers or adapters to supply any required restriction sites. Promoters for use in bacterial systems will also generally contain a Shine-Delgarno sequence operably linked to the DNA encoding the nucleic acid binding protein.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60–89, 1990). In the *E. coli* BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for overproduction of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcHisXpressTm (Invitrogen) or pTrc99 (Pharmacia Biotech, SE) or vectors containing the tac promoter such as pKK223-3 (Pharmacia Biotech) or PMAL (New England Biolabs, Mass., USA).

Moreover, the nucleic acid binding protein gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglyceraye mutase, pyruvate kinase, triose phosphate isomerase, phosphoglucose isomerase or glucokinase genes, or a promoter from the TATA binding, protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

Nucleic acid binding protein gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with nucleic acid binding protein sequence, provided such promoters are compatible with the host cell systems.

Transcription of a DNA encoding nucleic acid binding protein by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to nucleic acid binding protein DNA, but is preferably located at a site 5' from the promoter.

Advantageously, a eukaryotic expression vector encoding a nucleic acid binding protein according to the invention may comprise a locus control region (LCR). LCRs are capable of directing high-level integration site independent expression of transgenes integrated into host cell chromatin, which is of importance especially where the nucleic acid binding protein gene is to be expressed in the context of a permanently-transfected eukaryotic cell line in which chromosomal integration of the vector has occurred, or in transgenic animals.

Eukaryotic vectors may also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding nucleic acid binding protein.

An expression vector includes any vector capable of expressing nucleic acid binding protein nucleic acids that are operatively linked with regulatory sequences, such as promoter regions, that are capable of expression of such DNAs. Thus, an expression vector refers to a recombinant DNA or RNA construct, such as a plasmid, a phase, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding nucleic acid binding protein may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding nucleic acid binding protein in mammalian cells. Transient expression usually involves the use of an expression vector that is able to replicate efficiently in a host cell, such that the host cell accumulates many copies of the expression vector, and, in turn, synthesises high levels of nucleic acid binding protein. For the purposes or the present invention, transient expression systems are useful e.g. for identifying nucleic acid binding protein mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing nucleic acid binding protein expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing the nucleic acid binding protein. Suitable prokaryotes include eubacteria, such as Gram-negative or Gram-positive organisms, such as E. coli, e.g. E. coli K-12 strains, DH5a and HB101, or Bacilli. Further hosts suitable for the nucleic acid binding protein encoding vectors include eukaryotic microbes such as filamentous fungi or yeast, e.g. Saccharomyces cerevisiae. Higher eukaryotic cells include insect and vertebrate cells, particularly mammalian cells including human cells, or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of the nucleic acid binding protein-encoding nucleic acid to form the nucleic acid binding protein. The precise amounts of DNA encoding the nucleic acid binding protein may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby the nucleic acid binding protein encoded by the DNA is expressed. The composition of suitable media is known to those in the art, so that they can be readily prepared. Suitable culturing media are also commercially available.

The zinc finger polypeptides according to the present invention are varied at at least one position. Preferably, the positions selected for variation is one of the positions identified above as being important in determining the binding specificity of the zinc finger polypeptide of the invention.

By "vary" (including grammatical modifications) it is intended to denote that a particular amino acid in the molecule is replaced with an amino acid selected from a varied group, to produce a repertoire of homologous zinc finger polypeptides which differ at the particular amino acid position. The variant amino acids may be selected from a small group of two or more amino acids, from a larger group or may be completely randomly selected from all 20 naturally occurring amino acids. In a preferred embodiment, amino acid analogues and artificial amino acids may be employed.

Variation of the zinc finger binding motifs produced according to the invention is preferably directed to those residues where the code provided herein gives a choice of residues. For example, therefore, positions +1, +5 and +8 are advantageously randomised, whilst preferably avoiding hydrophobic amino acids: positions involved in binding to the nucleic acid, notably −1, +2, +3 and +6, may be randomised also, preferably within the choices provided by the rules of the present invention.

Preferably, therefore, the "default" protein produced according to the rules provided by the invention can be improved by subjecting the protein to one or more rounds of variation and selection within the specified parameters.

Mutagenesis of zinc finger polypeptides may be achieved by any suitable means. Preferably, the mutagenesis is performed at the nucleic acid level, for example by synthesising novel genes encoding mutant proteins and expressing these to obtain a variety of different proteins. Alternatively, existing genes can be themselves mutated, such by site-directed or random mutagenesis, in order to obtain the desired mutant genes.

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A. Innis, D. H. Gelfand, J. J. Sninsky, T. J. White (eds.), Academic Press, New York, 1990). Preferably, the commercially available Altered Site II Mutagenesis System (Promega) may be employed, according to the directions given by the manufacturer.

Selection of varied polypeptides according to the invention is carried out by polysome display (see Table 1). This technique relies on coupled transcription and translation of the coding sequences encoding the zinc finger polypeptides of the invention. This is achieved by preventing dissociation of the mRNA template and the polypeptide chain from the ribosome, such that the whole entity can be isolated as a polysome. Polysomes are then selected by binding the polypeptide to target nucleic acid, and mRNA eluted from those polysomes which display the desired binding characteristics.

TABLE I

The Polysome Display Procedure

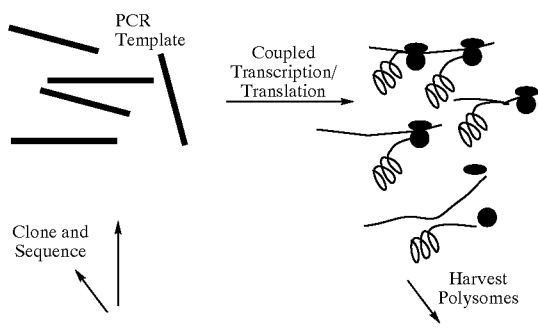

TABLE I-continued

The Polysome Display Procedure

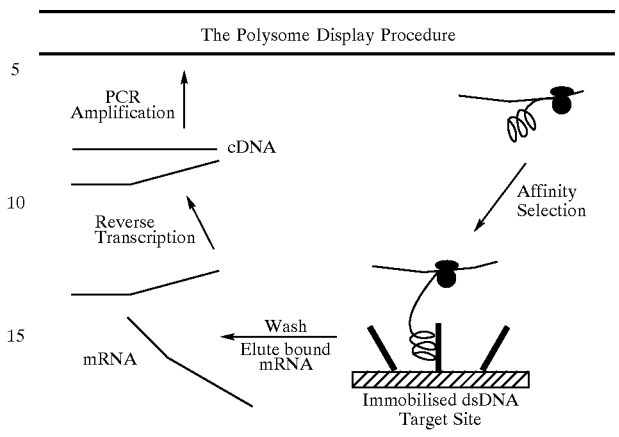

Polysome display may be performed according to the methods known in the art, as described below. For example, reference is made to WO95/11922, the methods of which are incorporated herein by reference. The methods of WO95/11922 may be adapted to the present invention, as follows:

Improved Methods For Screening Nascent Peptide Libraries

A polysome library displaying nascent zinc finger polypeptides can be generated by a variety of methods. Generally, an in vitro translation system is employed to generate polysomes from a population of added mRNA species. Often, the in vitro translation system used is a conventional eukaryotic translation system (e.g., rabbit reticulocyte lysate, wheat germ extract). However, an *E. coli* S30 system (Promega, Madison, Wis.) can be used to generate the polysome library from a population of added mRNA species or by coupled transcription/translation (infra). Suitable *E. Coli* S30 systems may be produced by conventional methods or may be obtained from commercial sources (Promega, Madison, Wis.). The *E. coli* S30 translation system is generally more efficient at producing polysomes suitable for affinity screening of displayed nascent peptides, and the like. Moreover, a prokaryotic translation system, such as the *E. coli* S30 system, has the further advantage that a variety of drugs which block prokaryotic translation (e.g., inhibitors of ribosome function), such as rifampicin or chloramphenicol, can be added at a suitable concentration and/or timepoint to stall translation and produce a population of stalled polysomes, suitable for affinity screening against a target nucleic acid sequence.

In general, the method comprises the steps of: (1) introducing a population of mRNA species into a prokaryotic in vitro translation system (e.g., *E. coli* S30) under conditions suitable for translation to form a pool of polysomes displaying nascent zinc finger polypeptides, so-called polysome forming conditions; (2) contacting the polysomes with a target nucleic acid under suitable binding conditions (i.e., for specific binding to the target nucleic acid and for preserving intact polysome structure); (3) selecting polysomes which are specifically bound to the nucleic acid (e.g., by removing unbound polysomes by washing with a solution); and (4) determining the polynucleotide sequences of the selected polysomes (e.g., by synthesizing cDNA or reverse transcriptase PCR amplification product, and sequencing said cDNA or amplification product). Often, the nucleic acid used for screening is immobilized, such as by being bound to a solid support.

In a variation of the method, the population of mRNA molecules is introduced into the in vitro translation system by de novo synthesis of the mRNA from a DNA template. In this improvement, a population of DNA templates capable of being transcribed in vitro (e.g., having an operably linked T7 or SP6 or other suitable promoter) are introduced into a coupled in vitro transcription/translation system (e.g., an E. coli S30 system) under conditions suitable for in vitro transcription and translation of the transcribed product. Generally, using a coupled in vitro transcription/translation system is highly efficient for producing polysomes displaying nascent zinc finger polypeptides suitable for affinity screening. Of course, and as noted above. uncoupled systems may also be used, i.e., by adding mRNA to an in vitro translation extract.

A further improvement to the general methods of screening nascent zinc finger polypeptide-displaying polysomes comprises the additional step of adding a preblocking agent (e.g., nonfat milk, serum albumin, tRNA, and/or gelatin) prior to or concomitant with the step of contacting the nascent peptide displaying polysomes with an immobilized nucleic acid. The additional step of adding a preblocking agent reduces the amount of polysomes which bind nonspecifically to the target nucleic acid and/or to the immobilization surface (e.g., microtitre well), thereby enhancing the specificity of selection for polysomes displaying peptides that specifically bind to the nucleic acid. Although the preblocking agent can be selected from a broad group of suitable compositions, the group of preblocking agents comprising: nonfat milk/nonfat milk solids, casein, bovine serum albumin, transfer RNA, and gelatin are preferred, with nonfat milk being especially preferable. Other suitable preblocking agents can be used.

Preblocking agents that do not substantially interfere with specific binding (i.e., non-interfering) are suitable.

A further improvement to the general methods of screening nascent peptide-displaying polysomes comprises the additional step of isolating polysomes from an in vitro translation reaction (or a coupled in vitro transcription/translation reaction) prior to the step of contacting the nascent peptide-displaying polysomes with nucleic acid. Generally, the polysomes are isolated from a translation reaction by high speed centrifugation to pellet the polysomes, so that the polysome pellet is recovered and the supernatant containing contaminants is discarded. The polysome pellet is resolubilised in a suitable solution to retain intact polysomes. The resolubilised polysomes may be recentrifuged at lower speed (i.e., which does not pellet polysomes) so that the insoluble contaminants pellet and are discarded and the supernatant containing soluble polysomes is recovered, and the supernatant used for affinity screening. Alternatively, the resolubilised polysomes may be used for affinity screening directly (i.e., without low speed centrifugation). Furthermore, the order of centrifugation may be reversed, so that low speed centrifugation is performed prior to high speed centrifugation; the low speed centrifugation supernatant is then centrifuged at high speed and the pelleted polysomes are resolubilised and used for affinity screening. Multiple rounds of high speed and/or low speed centrifugation may be used to increasingly purify the polysomes prior to contacting the polysomes with the immobilized nucleic acid.

Another improvement to the general methods of affinity screening of nascent peptide-displaying polysomes comprises adding a non-ionic detergent to the binding and/or wash buffers. Non-ionic detergent (e.g., Triton X-100, NP-40, Tween, etc.) is added in the binding buffer (i.e., the aqueous solution present during the step of contacting the polysomes with the immobilized nucleic acid) and/or the wash buffer (i.e., the aqueous solution used to wash the bound polysomes (i.e., bound to the immobilized nucleic acid). Generally, the non-ionic detergent is added to a final concentration of about between 0.01 to 0.5% (v/v), with 0.1% being typical.

Another improvement to the general methods of affinity screening of nascent peptide libraries is generating the DNA template library (from which the mRNA population is transcribed) in vitro without cloning the library in host cells. Cloning libraries in host cells frequently diminishes the diversity of the library and may skew the distribution of the relative abundance of library members. In vitro library construction generally comprises ligating each member of a population of polynucleotides encoding library members to a polynucleotide sequence comprising a promoter suitable for in vitro transcription (e.g., T7 promoter and leader). The resultant population of DNA templates may optionally be purified by gel electrophoresis. The population of DNA templates is then transcribed and translated in vitro, such as by a coupled transcription/translation system (e.g., E. coli S30).

A further improvement to the general methods of affinity screening comprises the added step of combining affinity screening of a nascent peptide-displaying polysome, library with screening of a bacteriophage peptide display library (or other, i.e., peptides on plasmids, expression as secreted soluble antibody in host cells, in vitro expression). In this improvement, polysomes are isolated by affinity screening of a nascent peptide-display library. The isolated polysomes are dissociated, and cDNA is made from the mRNA sequences that encoded nascent peptides that specifically bound to the target nucleic acid). The cDNA sequences encoding the nascent peptide binding regions (i.e., the portions which formed binding contacts to the nucleic acid(s); variable segment sequences) are cloned into a suitable bacteriophage peptide display vector (e.g., pAFF6 or other suitable vector). The resultant bacteriophage vectors are introduced into a host cell to produce a library of bacteriophage particles. Each of the phage clones express on their virion surface the polysome derived peptide sequences as fusions to a coat protein (e.g., as an N-terminal fusion to the PIII coat protein). By incorporating the in vitro-enriched peptide sequences from the polysome screening into a bacteriophage display system, it is possible to continue affinity selection for additional rounds. It is also advantageous, because the resultant bacteriophage display libraries can be screened and tested under conditions that might not have been appropriate for the intact polysomes.

Another improvement to the methods of affinity screening is the control of display valency (i.e., the average number of functional zinc finger polypeptides displayed per polysome, and the capacity to vary display valency in different rounds of affinity screening. Typically, a high display valency permits many binding contacts between the polysome and nucleic acid, thus affording stable binding for polysomes which encode zinc finger polypeptide species which have relatively weak binding. Hence, a high display valency system allows screening to identify a broader diversity range of zinc finger polypeptides, since even lower affinity zinc finger polypeptides can be selected. Frequently, such low-to-medium affinity zinc finger polypeptides can be superior candidates for generating very high affinity zinc finger polypeptides, by selecting high affinity zinc finger polypeptides from a pooi of mutagenised low-to-medium affinity zinc finger clones. Thus, affinity sharpening by mutagenesis and subsequent rounds of affinity selection can be used in conjunction with a broader pool of initially selected zinc finger polypeptide sequences if a high display valency method is used. Alternate rounds of high display valency screening and low display valency screening can be performed, in any order, starting from either a high or low valency system, for as many affinity screening rounds as desired, with intervening variation and sequence diversity broadening, if desired. Alternate rounds of affinity screening, wherein a first round consists of screening a zinc finger polypeptide library expressed in a high valency system, selecting zinc finger polypeptide clones which bind the target nucleic acid, optionally conducting a mutagenesis step to expand the sequence variability of the selected zinc finger polypeptides, expressing the selected zinc finger polypeptide clones in a lower valency display system, and selecting clones which bind the target nucleic acid, can be performed, including various permutations and combinations of multiple screening cycles, wherein each cycle can be of a similar or different display valency. This improvement affords an overall screening program that employs systems which are compatible with switchable valency (i.e., one screening cycle can have a different display valency than the other(s), and can alternate in order).

Display valency can be controlled by a variety of methods, including but not limited to: controlling the average number of nascent peptides per polysome in a polysome-display system. This can be controlled by any suitable method, including: (1) altering the length of the encoding mRNA sequence to reduce or increase the frequency of translation termination (a longer mRNA will typically display more nascent peptides per polysome than a shorter mRNA encoding sequence), (2) incorporating stalling (i.e., infrequently used) codons in the encoding mRNA, typically distal (downstream of) of the zinc finger polypeptide-encoding portion(s), (3) incorporating RNA secondary structure-forming sequences (e.g., hairpin, cruciform, etc.) distal to the zinc finger polypeptide-encoding portion and proximal to (upstream to) the translation termination site, if any, and/or (4) including an antisense polynucleotide (e.g., DNA, RNA, polyamide nucleic acid) that hybridizes to the mRNA distal to the zinc finger polypeptide-encoding portion and proximal to (and possibly spanning the translation termination site, if any. The length of the mRNA may be increased to increase display valency, such as by adding additional reading frame sequences downstream of the zinc finger polypeptide-encoding sequences; such additional reading, frame sequences can, for example, encode the sequence (-AAVP-)$_n$, where n is typically at least 1, frequently at least 5 to 10, often at least 15 to 25, and may be at least 50–100, up to approximately 150 to 500 or more, although infrequently a longer stall sequence can be used. Stalling codons (i.e., codons which are slowly translated relative to other codons in a given translation system) can be determined empirically for any translation system, such as by measuring translation efficiency of mRNA templates which differ only in the presence or relative abundance of particular codons. For example, a set of clones can be evaluated in the chosen translation system; each species or the set has a stalling polypeptide sequence of 25 amino acids, but each stalling polypeptide sequence consists of a repeating series of one codon, such that all translatable codons are represented in the set. When translated under equivalent conditions, the zinc finger polypeptide species which produce polysomes having the highest valency (e.g., as determined by sedimentation rate, buoyancy, electron microscopic examination, and other diagnostic methods) thereby identify stalling codons as the codon(s) in the stalling polypeptide sequence.

In one embodiment, a stalling polypeptide sequence is distal (3' to) the zinc finger polypeptide-encoding sequence, and comprises -(Gly-Gly-Gly-Gly-Ser)-A-A-V-P-, or repeats thereof.

Alternatively, or in combination with the noted variations, the valency of the target nucleic acid may be varied to control the average binding affinity of selected library members. The target nucleic acid can be bound co a surface or substrate at varying densities, such as by including a competitor tarhet nucleic acid, by dilution, or by other method known to those in the art. A high density (valency) of target nucleic acid can be used to enrich for library members which have relatively low affinity, whereas a low density (valency) can preferentially enrich for higher affinity library members.

Each of the improvements to the methods of affinity screening may be combined with other compatible improvements. For example, an in vitro transcription/translation system can be used in conjunction with a library of DNA templates synthesized in vitro (i.e. without cloning in a host cell). The resultant polysomes can be purified by one or more rounds of high-speed and/or low-speed centrifugation. The purified polysomes can be contacted with an immobilized nucleic acid that is preblocked (e.g., with nonfat milk), and a non-ionic detergent may also be present to further reduce nonspecific binding. The selected polysomes may then be used as templates for synthesizing cDNA which is then cloned into a bacteriophage display vector, such that the variable segments of the nascent peptides are now displayed on bacteriophage.

Amplification, Affinity Enrichment, And Screening

A basic method is described for synthesizing a nascent peptide-polysome library in vitro, screening and enrichment of the library for species having desired specific binding properties, and recovery of the nucleotide sequences that encode those peptides of sufficient binding affinity for target nucleic acid sufficient for selection by affinity selection.

The library consists of a population of nascent zinc finger polypeptide library members comprising nascent peptides. After selecting those nascent peptide library members that bind to the nucleic acid with high affinity, the selected complexes are disrupted and the mRNA is recovered and amplified to create DNA copies of the message. Typically each copy comprises an operably linked in vitro transcription promoter (e.g., T7 or SP6 promoter). The DNA copies are transcribed in vitro to produce mRNA, and the process is repeated to enrich for zinc finger polypeptides that bind with sufficient affinity.

The following general steps are frequently followed in the method: (1) generate a DNA template which is suitable for in vitro synthesis of mRNA, (2) synthesize mRNA in vitro by transcription of the DNA templates in a coupled transcription/translation system, (3) bind the nascent peptide to a preferably immobilised target nucleic acid, (4) recover and amplify nascent peptide library members which bind the target nucleic acid and produce DNA templates from the selected library members competent for in vitro transcription.

Each generated DNA template preferably contains a promoter (e.g., T7 or SP6) which is active in an in vitro transcription system. A DNA template generally comprises (1) a promoter which is functional for in vitro transcription and operably linked to (2) a polynucleotide sequence encoding an mRNA period. Said encoded mRNA comprises a polynucleotide sequence which encodes a polypeptide comprising a zinc finger polypeptide, (2) a polynucleotide sequence to which a DNA primer suitable for priming first-strand cDNA synthesis of the mRNA can bind, and (3) a ribosome-binding site and other elements necessary for in vitro translatability of the mRNA, and optionally, for mRNA stability and translatable secondary structure, if any.

Following translation, polysome complexes are screened for high-affinity nucleic acid-binding using standard procedures and as described herein.

After selecting those nascent peptide/polynucleotide complexes that bind with sufficient affinity, the polysomes are isolated and ribosomes released by the addition of EDTA sufficient to chelate the Mg+2 present in the buffer. Ribosomes are removed by high-speed centrifugation, and the RENA component is released by phenol extraction, or by changing the ionic strength, temperature or pH of the binding buffer so as to denature the nascent peptide. A cDNA copy of the mRNA is made using reverse transcriptase, and the cDNA copy is amplified by, the polymerase chain reaction (PCR). The amplified cDNA is added to the in vitro transcription system and the process is repeated to enrich for those peptides that bind with high affinity.

The invention is further described, for the purposes of illustration only, in the following examples.

EXAMPLE 1
Preparation of a Varied Zinc Finger Polypeptide

Zinc finger polypeptides incorporating variation at selected positions are constructed in accordance with the preceding instructions, or as described in any one of GB9710805.4, GB9710806.2, GB9710807.0, GB9710808.8, GB9710809.6, GB9710810.4, GB9710811.2, GB9710812.0 or EP95928576.8, which are incorporated herein by reference.

EXAMPLE 2
The Template Construct

The construct is similar to that of Mattheakis et al (1994) Proc Natl Acad Sci USA, 91, 9022–9026, but with some modifications to increase the efficiency of ribosome stalling.

General Structure

The general structure of a transcription template suitable for selection of zinc finger polypeptides according to the present invention is shown in Table 2.

TABLE 2

General Structure of Zinc Finger Transcription Unit

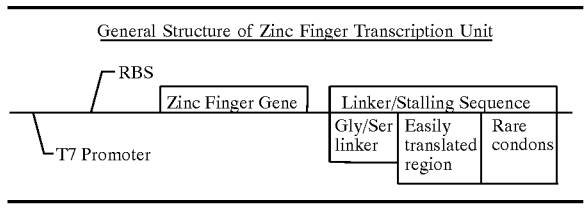

The unit contains a bacteriophage T7 RNA polymerase promoter, which drives a coding sequence encoding a zinc finger polypeptide. Appended to the coding, sequence is a linker/stalling sequence region which comprises a flexible Gly/Ser linker, an easily translatable region and a stalling region which is composed of codons rare in *E. coli*. Rare codons hold up the translation process and effectively stall the ribosome on the template.

Sequence Information

T7 Promoter

This is the standard bacteriophage T4 RNA polymerase promoter, having the sequence TAATA CGA CTA ACT ATA GGG AGA (SEQ ID NO:13).

Ribosome Binding Site

This is the bacteriophage T7, gene 10 ribosome binding site. (This and the T7 promoter give high efficiency initiation of transcription and translation). It has the sequence AAG-GAG.

Zinc Finger Gene

A zinc finger coding sequence as shown in SEQ. ID. No. 1 is used.

Linker/Stalling Sequence

The first ¾ of this sequence is virtually the same as that used by Mattheakis et al (1994). This is because it is the principles behind the design which are important, and not the sequence itself.

First there is a 31 residue serine-glycine repeat. This serves as a flexible linker, when translated, which ensures that the expressed zinc finger construct has spacial separation, and flexibility with respect to the stalled ribosome.

Second there is a series of Ala-Ala-Val-PrO (residues 21–24 of SEQ ID NO:12) repeats. This is a standard, relatively easily translated sequence and serves to ensure that the ribosome is stalled after (and not before) the entire flexible (Ser-Gly) linker has emerged from the ribosome. This is relatively important since approximately ten amino acids are covered by the ribosome at any one time.

Third comes a short stretch of codons which contain a high proportion of rare codons—with respect to *E. coli* usage, which slow the translational process and cause regular pauses.

Fourth, there is added towards the end of the "third region" an additional ribosome stalling sequence. This has been discussed in Gu et al (1994) Proc Natl Acad Sci USA, 91, 5612–5616 and Lovett & Rogers (1996) Microbiological Reviews, 60, 366–385.

The sequence:

```
    M   V   T   D   K       (SEQ ID NO:16)
   ATG GTT AAA ACA GAT AAA   (SEQ ID NO:15)
``` when translated, interacts with the peptidyl transferase site of the *E. coli* ribosome, causing translational pausing. In the presence of chloramphenicol, this paused state becomes a stalled state.

The sequence is found at the beginning of the cat-86 gene in *E. coli* which gives resistance to this antibiotic It has been found that this sequence increases the efficiency of ribosome stalling by between 10% and 20%, when compared to the exact sequence used by Mattheakis et al (1994).

Finally, there is no translational STOP codon, so ribosomes will pause when they reach the end of the RNA transcript, before dissociating.

EXAMPLE 3
The Procedure

The template used is produced by PCR and so is linear, double-stranded DNA of approximately 670 bps.

Transcription is carried out in a coupled transcription and translation system for linear DNA templates. (The *E. coli* 530 extract system for linear DNA-Promega.)

At present, transcription/translation reactions are carried out in 50 µl volumes, each primed with approximately one pmole template—(400–500 ng, up to $10^{12}$ DNA molecules).

The extract system does not contain T7 RNA polymerase, so this is supplemented by adding T7 polymerase enzyme, and endogenous *E. coli* RNA polymerase is inhibited by adding rifampicin.

| | | |
|---|---|---|
| Template (0.5 pM/µl) | 2 µl | |
| Rifampicin (50 µg/nl) | 1 | inhibits *E. coli* RNA polymerase |
| BZA (100 mM) | ½ | inhibits proteases |
| ZnCl₂ (20 mM) | 1 ¼ | 500 µM final concentration, for zinc finger folding |
| Amino acid mix | 5 | |
| 530 Premix | 20 | |

-continued

| 530 Extract | 15 | |
|---|---|---|
| RNasIN | ½ | inhibits RNases |
| T7 RNA polymerase | 1 (≧1000 U) | |
| H₂O | 3 ¾ | |
| | 50 µl | | incubate at 25° C./30 minutes.
add tress volumes of ice cold stalling buffer.
place on ice/15 minutes.

Incubation is carried out at 25° C., to help inhibit proteases and RNases, but can be done at any temperature up to 37° C.

The ribosomes are stalled by adding to the in vitro synthesis system three volumes of "stalling/polysome buffer".

Stalling/Polysome Buffer

This is made at 1⅓×concentrate but its 1×working concentrations are:

| Tris (pH 7.4) | 20 mM |
|---|---|
| KCl | 50 mM |
| MgCl₂ | 10 mM |
| DTT | 5 mM |
| ZnCl₂ | 50 µM |
| Chloramphenicol | 18 µg/ml |

The actual ingredients, as far as ribosome stalling is concerned, are $Mg^{2+}$ and Chloramphenicol. High $Mg^{2+}$ concentration (i.e. 10–20 mM) greatly increases the affinity of ribosomes for mRNA (Holschuh & Gassen. (1982) J Biol Chem, 257, 1987–1992) and chloramphenicol causes ribosomes to stall, particularly strongly when combined with the MVKTDK sequence. Tests show that up to 50% of mRNA is attached to ribosomes after stalling cf 40% when using the construct of Mattheakis et al, 1994.

To collect "polysomes":
spin 90,000 rpm/30 minutes/4° C. (all steps from here to the RT-PCR are carried out in the cold room).
resuspend polysome pellet in 200 µl of stalling buffer.
incubate on rolling mixer for 20 minutes/4° C.
spin down 13,000 rpm/5 minutes (to pellet insoluble material).
spin down 13,000 rpm/5 minutes (to pellet insoluble material).
collect supernatant.

EXAMPLE 4

Affinity Selection Of Polysomes

The target ds DNA binding site is pre-bound to streptavidin coated wells to give approximately 1 mM concentration once polysomes are added.

To 200 µl polysomes suspension, add 1 µg poly d(I-C) competitor DNA
immediately add to binding site coated wells.
incubate 30 minutes.
wash 6 times with "washing buffer".

Washing Buffer

This is 1× "stalling buffer", with the addition of 0.1% between 20 and twice the concentration of KCl and MgCl₂, to help remove non-specifically bound proteins.
wash 2 times with 1× stalling buffer.
add 100 µl of elution buffer.
incubate 30 minutes with gentle and occasional agitation Elution Buffer This is the same as stalling buffer, but without chloramphenicol or MgCl₂, and with the addition of 20 mM EDTA. The EDTA chelates $Mg^{2+}$ ions and dissociates ribosomes.

Removal Of DNA Contamination

To ensure that the next round of selection is not contaminated by template from the previous round, all ds DNA is removed by incubation with DNaseI.

To 100 µl eluted mRNA:
add 4 µl 1M MgCl₂ (since DNaseI requires $Mg^{2+}$)
add 2U DNaseI
incubate 37° C./15 minutes
phenol extract
ethanol precipitate mRNA
resuspend in 20 µl H₂O.

Reverse Transcription

Reverse transcription is then used to create a ss DNA template from the mRNA collected.

PCR

The ss DNA is then amplified by PCR to give a double-stranded, full-length template which can be used in the next round of selection experiments.

What is claimed is:

1. A method for producing a zinc finger nucleic acid binding protein comprising preparing a zinc finger protein according to design rules, varying the protein at one or more positions, and selecting variants that bind to a target nucleic acid sequence by polysome display.

2. The method according to claim 1, wherein the protein is varied at one or more positions selected from the group consisting of +1, +5, +8, −1, +2, +3, and +6.

3. The method of claim 1, wherein the design rules comprise:
   (i) preparing a nucleic acid binding protein of the Cys2-His2 zinc finger class capable of binding to a nucleic acid triplet in a target nucleic acid sequence, wherein binding to each base of the triplet by an α-helical zinc finger nucleic acid binding motif in the protein is determined as follows:
   a) if the 5' base in the triplet is G, then position +6 in the α-helix is Arg; or position +6 is Ser or Thr and position ++2 is Asp;
   b) if the 5' base in the triplet is A, then position +6 in the α-helix is Gln and ++2 is not Asp;
   c) if the 5' base in the triplet is T, then position +6 in the α-helix is Ser or Thr and position ++2 is Asp;
   d) if the 5' base in the triple is C, then position +6 in the α-helix may be any amino acid, provided that position ++2 in the α-helix is not Asp;
   e) if the central base in the triplet is G, then position +3 in the α-helix is His;
   f) if the central base in the triplet is A, then position +3 in the α-helix is Asn;
   g) if the central base in the triplet is T, then position +3 in the α-helix is Ala, Ser or Val; provided that if it is Ala, then one of the residues at −1 or +6 is a small residue;
   h) if the central base in the triplet is C, then position +3 in the α-helix is Ser, Asp, Glu, Leu, Thr or Val;
   i) if the 3' base in the triplet is G, then position −1 in the α-helix is Arg;
   j) if the 3' base in the triplet is A, then position −1 in the α-helix is Gln;
   k) if the 3' base in the triplet is T, then position −1 in the α-helix is Asn or Gln;
   l) if the 3' base in the triplet is C, then position −1 in the α-helix is Asp;
   (ii) varying the resultant polypeptide at at least one position; and
   (iii) selecting the variants which bind to a target nucleic acid sequence by polysome display.

4. The method of claim 3, wherein the or each zinc finger has the general primary structure $$X^a \ C \ X_{2-4} \ C \ X_{2-3} \ F \ X^c \ X \ X \ X \ X \ L \ X \ X \ H \ X \ X \ X^b \ \text{H-linker} \quad (A)$$
$$\phantom{X^a \ C \ X_{2-4} \ C \ X_{2-3} \ F \ X^c} \ {-1} \ 1 \ 2 \ 3 \ 4 \ 5 \ 6 \ 7 \ 8 \ 9$$

wherein X (including $X^a$, $X^b$ and $X^c$) is any amino acid.

5. The method according to claim 4, wherein $X^a$ is F/Y-X or P-F/Y-X.

6. The method according to claim 4, wherein $X_{2-4}$ is selected from any one of: S-X, E-X, K-X, T-X, P-X and R-X.

7. The method according to claim 4 wherein $X^b$ is T or I.

8. The method according to claim 4 wherein $X_{2-3}$ is G-K-A, G-K-C, G-K-S, G-K-G, M-R-N or M-R.

9. The method according to claim 4 wherein the linker is T-G-E-K or T-G-E-K-P.

10. The method according to claim 4 wherein position +9 is R or K.

11. The method according to claim 4 wherein positions +1, +5 and 8 are not occupied by any one of the hydrophobic amino acids F, W or Y.

12. The method according to claim 11 wherein positions +1, +5 and +8 are occupied by the residues K, T and Q, respectively.

13. The method according to claim 4 wherein the polysome display technique comprises the steps of:
   (a) introducing a population of mRNA species into an in vitro translation system under conditions suitable for translation to form a pool of polysomes displaying nascent zinc finger polypeptides;
   (b) contacting the polysomes with a target nucleic acid under suitable binding conditions;
   (c) selecting polysomes which are specifically bound to the nucleic acid; and
   (d) reverse transcribing and amplifying the isolated mRNA.

* * * * *